United States Patent [19]

Blair

[11] Plant 5,106

[45] Sep. 20, 1983

[54] *POTENTILLA FRUTICOSA* — BLINK VARIETY

[75] Inventor: Robert Blair, Dawyck Gardens, Scotland

[73] Assignee: The Conard-Pyle Company, West Grove, Pa.

[21] Appl. No.: 341,104

[22] Filed: Jan. 20, 1982

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Burns, Doane, Swecker & Mathis

EXEMPLARY CLAIM

A new and distinct variety of *Potentilla fruticosa* is provided. The new variety was formed by crossing the Tangerine variety with an unknown pollen parent, and possesses a distinctive true pink flower coloration which can be readily distinguished from the blossom colorations of the Red Ace and Royal Flush varieties.

2 Drawing Figures

SUMMARY OF THE INVENTION

A hardy relatively disease free new variety of *Potentilla fruticosa* is provided which unlike many other plants of the species possesses a distinctive flower coloration. For instance, heretofore most *Potentilla fruticosa* plants have tended to produce blossoms which are white, creamy white, yellow, red, etc. A true pink variety has not been known.

The new and distinct variety of *Potentilla fruticosa* originated at Dawyck, Scotland, United Kingdom during 1973 by crossing plants of the Tangerine variety (non-patented) with pollen from an unknown pollen parent. The resulting seed was sown during 1973 and the plants produced first flowered during 1974. A single plant of the present variety was selected because of its distinctive flower coloration.

The new variety was found to exhibit attractive pink blossoms which are a truer pink than those of the Royal Flush variety (i.e. U.S. Plant Pat. No. 4,628), and to exhibit a more vigorous and a more upright growth habit than such variety. Also, the blossoms can be readily distinguished from red flowers of the Red Ace variety (i.e. U.S. Plant Pat. No. 4,226). In other respects the new variety is believed to be substantially identical to other *Potentilla fruticosa* plants such as the Royal Flush and Red Ace varieties. For instance, the new variety is hardy and relatively disease free and is suitable for growing as an attractive ornamental landscape planting.

Asexual reproduction by cuttings has confirmed that the distinguishing characteristics are uniformly transmitted to succeeding generations.

BRIEF DESCRIPTION OF THE PHOTOGRAPH

The accompanying photographs show typical specimens of the established plants of the new variety grown outdoors at Norfolk, England, United Kingdom during the late summer as depicted in color as nearly true as it is reasonably possible to make the same in color illustrations of this character. The attractive true pink blossoms are apparent.

FIG. 1 illustrates the overall appearance of the plant while blossoming, and FIG. 2 illustrates the pink blossoms in greater detail.

DETAILED DESCRIPTION OF THE NEW VARIETY

Figure 1:
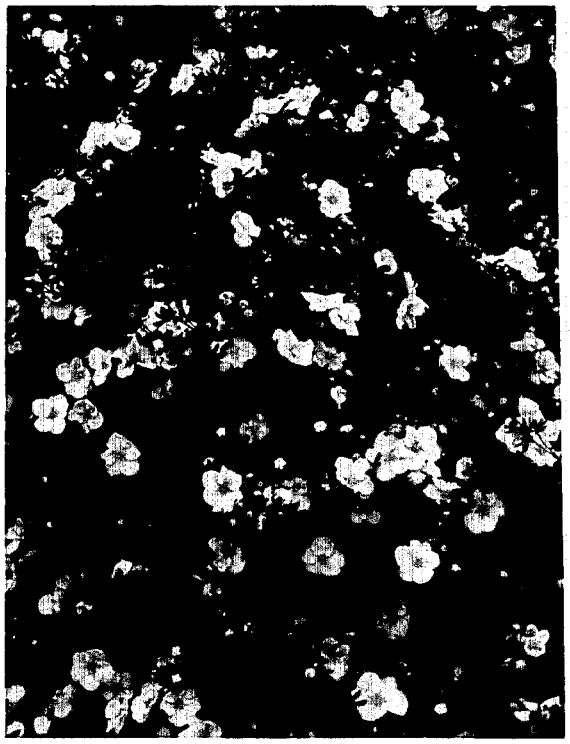
Figure 2:
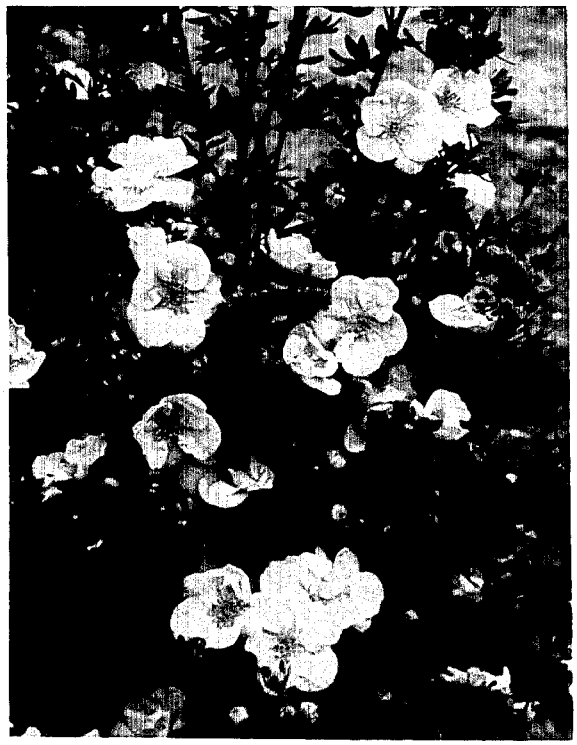

The following description was made from established plants of the new variety of *Potentilla fruticosa* growing outside at Norfolk, England, United Kingdom during June, 1981.

The chart used in the identification of the colors is that of The Royal Horticultural Society (R.H.S. Colour Chart).

Bloom:

*Flowers borne.*—Several per stem on relatively short stems.

*Quantity of bloom.*—Free when grown outside.

*Continuity.*—Intermittent.

*Bloom size.*—Small, approximately 25 to 35 mm. on average when fully open.

*Petalage.*—Round, single (i.e. one row of petals).

*Petal appearance.*—Satiny on inside and outside. The true pink coloration described hereafter may tend to fade to almost white during periods of hot and dry weather.

*Color of newly opened flower — outside surface.*—White.

*Color of newly opened flower — inside surface.*—Pink, Red Group 55C.

*Color when open three days — outside surface.*—Light pink, Red Group 56D. This color tends to be maintained throughout the remaining life of the flower unless the weather is hot and dry.

*Color when open three days — inside surface.*—White flushed with pink, Red Group 56B. Towards the end of the life of the flower this coloration changes to white flushed with a lighter pink, Red Group 56C.

Foliage:

*Leaves.*—Compound of usually five leaflets. The shape is ovoid with an acute apex and an obtuse base.

*Color of young leaves.*—The upper and under surfaces are a medium green, Green Group 143C.

*Color of mature leaves.*—The upper surface is a darker green, Yellow-Green Group 146B, and the under surface is a similar green, Yellow-Green Group 146C.

Reproductive organs:

*Stamens.*—Many.

*Filaments.*—Up to approximately 2.3 mm. long with anthers. The coloration corresponds to Yellow Group 6C.

*Anthers.*—Approximately 1×1.5 mm. in size. The coloration corresponds to Yellow-Orange Group 14B.

*Pistils.*—Many.

*Styles.*—Very uneven, and very loosely separated.

*Stigma.*—Yellow.

*Ovaries.*—All enclosed in receptacle.

*Sepals.*—Approximately 6 mm. long.

*Seeds.*—Medium number and small.

I claim:

1. A new and distinct variety of *Potentilla fruticosa* substantially as herein shown and described which exhibits (a) attractive pink blossoms which are a truer pink than those of the Royal Flush variety, (b) a more vigorous growth than the Royal Flush variety, and (c) a more upright growth habit than the Royal Flush variety.

* * * * *